(12) United States Patent
Bradway et al.

(10) Patent No.: US 10,709,544 B2
(45) Date of Patent: Jul. 14, 2020

(54) NON-CYLINDRICAL VARIABLE PITCH MESH TOP STENT

(71) Applicants: Cook Medical Technologies LLC, Bloomington, IN (US); Emily Bell Gibbons, Bloomington, IN (US)

(72) Inventors: Ryan C. Bradway, Tacoma, WA (US); Jarin A. Kratzberg, Lafayette, IN (US); William S. Gibbons, Jr., Bloomington, IN (US)

(73) Assignee: Cook Medical Technologies LLC, Bloomington, IN (US)

( * ) Notice: Subject to any disclaimer, the term of this patent is extended or adjusted under 35 U.S.C. 154(b) by 34 days.

(21) Appl. No.: 16/038,848

(22) Filed: Jul. 18, 2018

(65) Prior Publication Data

US 2019/0021842 A1 Jan. 24, 2019

Related U.S. Application Data

(60) Provisional application No. 62/534,497, filed on Jul. 19, 2017.

(51) Int. Cl.
*A61F 2/07* (2013.01)
*A61F 2/90* (2013.01)
(Continued)

(52) U.S. Cl.
CPC .............. *A61F 2/07* (2013.01); *A61F 2/90* (2013.01); *A61F 2/88* (2013.01); *A61F 2/92* (2013.01);
(Continued)

(58) Field of Classification Search
CPC ...... A61F 2/92; A61F 2/07; A61F 2/89; A61F 2/90; A61F 2/88; A61F 2002/061;
(Continued)

(56) References Cited

U.S. PATENT DOCUMENTS 6,099,558 A  8/2000 White et al.
7,771,466 B2  8/2010 Chouinard et al.
(Continued)

FOREIGN PATENT DOCUMENTS

CN  102125475 A  7/2011
DE  102014115337 A1  4/2016
(Continued)

OTHER PUBLICATIONS

Qingsheng Lu, et al., "Endovascular Repair of Ascending Aortic Dissection—A Novel Treatment Option for Patients Judged Unfit for Direct Surgical Repair," *Clinical Research: Vascular Disease*, vol. 61, Issue 18, May 2013, 8 pages.
(Continued)

*Primary Examiner* — Thomas Sweet
*Assistant Examiner* — Tiffany P Shipmon
(74) *Attorney, Agent, or Firm* — Brinks Gilson & Lione (57) ABSTRACT

A stent is provided having a plurality of intersecting elongated members arranged to form a plurality of cells, which define an elongated tube with a lumen. The elongated tube has first and second sections, the first section having a substantially constant first diameter, the second section having a substantially constant second diameter that is larger than the first diameter. The elongated tube also has a transition section between the first and second sections, the transition section having a concave curvature extending proximally from the first section and a convex curvature extending proximally from the concave curvature to the second portion. A proximal end of the second section has a plurality of rounded ends formed by the plurality of intersecting elongated members. Each of the plurality of cells within the first section have a pitch that is tighter than each of the plurality of cells within the second section.

24 Claims, 7 Drawing Sheets

(51) Int. Cl.
*A61F 2/88* (2006.01)
*A61F 2/92* (2013.01)
*A61F 2/82* (2013.01)

(52) U.S. Cl.
CPC . *A61F 2002/823* (2013.01); *A61F 2230/0004* (2013.01); *A61F 2230/0065* (2013.01); *A61F 2230/0069* (2013.01); *A61F 2250/0018* (2013.01); *A61F 2250/0039* (2013.01)

(58) Field of Classification Search
CPC .......... A61F 2002/067; A61F 2002/826; A61F 2230/0019; A61F 2240/001
See application file for complete search history.

(56) References Cited

U.S. PATENT DOCUMENTS

| | | | |
|---|---|---|---|
| 8,002,816 B2 | 8/2011 | Greenberg | |
| 8,956,400 B2 | 2/2015 | Beach et al. | |
| 2006/0195172 A1 | 8/2006 | Luo et al. | |
| 2007/0043435 A1 | 2/2007 | Seguin et al. | |
| 2007/0073388 A1 | 3/2007 | Krolik et al. | |
| 2007/0179590 A1* | 8/2007 | Lu | A61F 2/07 623/1.16 |
| 2008/0319552 A1 | 12/2008 | Styrc | |
| 2009/0270965 A1 | 10/2009 | Sinha et al. | |
| 2011/0060398 A1* | 3/2011 | Tupil | A61F 2/07 623/1.15 |
| 2011/0093002 A1 | 4/2011 | Rucker et al. | |
| 2012/0046726 A1 | 2/2012 | Chuter | |
| 2014/0060691 A1 | 3/2014 | Du | |
| 2014/0277370 A1 | 9/2014 | Brocker et al. | |
| 2014/0277573 A1* | 9/2014 | Gill | A61F 2/90 623/23.68 |
| 2014/0296966 A1 | 10/2014 | Braido et al. | |
| 2014/0316513 A1 | 10/2014 | Tang | |
| 2015/0148883 A1 | 5/2015 | Hyodoh | |
| 2015/0157477 A1 | 6/2015 | Shahriari | |
| 2017/0304093 A1* | 10/2017 | During | A61F 2/90 |

FOREIGN PATENT DOCUMENTS

| | | |
|---|---|---|
| EP | 2005918 A1 | 12/2008 |
| EP | 3326582 A1 | 5/2018 |
| WO | WO 2009/094188 A2 | 7/2009 |

OTHER PUBLICATIONS

European Search Report for corresponding EP Application No. 18275101, dated Nov. 21, 2018, 9 pages.
European Search Report for related EP Application No. 18275102, dated Nov. 21, 2018, 8 pages.

\* cited by examiner

NON-CYLINDRICAL VARIABLE PITCH MESH TOP STENT

RELATED APPLICATIONS

The application claims the benefit of the filing date under 35 U.S.C. § 119(e) of Provisional U.S. Patent Application Ser. No. 62/534,497, filed Jul. 19, 2017, which is hereby incorporated by reference in its entirety.

FIELD

The present disclosure relates to medical devices and more specifically to stents used to treat a diseased vessel or region of vessels.

BACKGROUND

The statements in this section merely provide background information related to the present disclosure and may not constitute prior art.

The functional vessels of human and animal bodies, such as blood vessels and ducts, occasionally weaken or even rupture. For example, the aortic wall can weaken, resulting in an aneurysm. Upon further exposure to hemodynamic forces, such an aneurysm can rupture, resulting in an aortic dissection.

One treatment option for weakened, aneurysmal, or ruptured vessels is the use of stent grafts, placed either surgically or endovascularly. A stent graft may be, for example, a tubular structure that is placed into a body lumen, such as the aorta, to, for example, span a weakened area or to maintain patency of the body lumen. When treating aortic aneurysms or dissections, a stent graft is generally placed within the damaged portion of the aorta to bypass the weakened area of the aorta or to seal a tear (dissection) in the aorta, thereby reestablishing a closed pathway for blood to flow through.

While aortic aneurysms and dissections can occur along the length of the aorta, they are particularly difficult to treat when occurring in the ascending aorta near the sinotubular junction. Conventional seal stents often do not provide an adequate seal near the sinotubular junction because of its unusual anatomy. While the ascending aorta is substantially cylindrical in shape, the sinotubular junction marks a transition point from this cylindrical anatomy to the annular shape of the aortic root. Thus, the transition point of the sinotubular junction sees an anatomical change in both size and diameter. Due to these anatomical changes, stent grafts positioned near the sinotubular junction have issues with leakage and sufficient sealing of the aorta. Thus, it is desirable to provide a stent graft that can provide an adequate seal in the ascending aorta near the sinotubular junction.

SUMMARY OF THE INVENTION

The present invention seeks to provide an improved stent and stent graft. In one form of the present disclosure, a stent is provided comprising a plurality of intersecting elongated members arranged to form a plurality of cells, the plurality of cells defining an elongated tube with a lumen running therethrough. Further, the elongated tube comprises first and second sections, the first section having a substantially constant first diameter, the second section having a substantially constant second diameter that is larger than the first diameter. The elongated tube further comprises a transition section between the first and second sections, the transition section having a concave curvature extending proximally from the first section and a convex curvature extending proximally from the concave curvature to the second portion. Further, a proximal end of the second section comprises a plurality of rounded ends formed by the plurality of intersecting elongated members. Also, each of the plurality of cells within the first section have a pitch that is tighter than each of the plurality of cells within the second section.

According to another aspect of the present invention, a stent graft is provided comprising a graft comprising an elongate body with a lumen running therethrough. The stent graft further comprises a stent attached to the graft, wherein the stent comprises a plurality of intersecting elongated members arranged to form a plurality of cells, the plurality of cells defining an elongated tube with a lumen running therethrough. The elongated tube comprises first and second sections, the first section having a substantially constant first diameter, the second section having a diameter transitioning from the first diameter of the first section to a second diameter that is larger than the first diameter. In addition, each of the plurality of cells within the first section have a pitch that is tighter than each of the plurality of cells within the second section. Further, the graft covers the first section of the stent but not the second section.

There is also described a method of placing a stent comprising introducing a stent graft into an aorta of a patient with the stent graft in a compressed, delivery configuration. The stent graft comprises a stent comprising a plurality of intersecting elongated members arranged to form a plurality of cells, the plurality of cells defining an elongated tube with a lumen running therethrough. The elongated tube comprises first and second sections, the first section having a substantially constant first diameter, the second section having a substantially constant second diameter that is larger than the first diameter. The elongated tube further comprises a transition section between the first and second sections, the transition section having a concave curvature extending proximally from the first section and a convex curvature extending proximally from the concave curvature to the second portion. Further, each of the plurality of cells within the first section have a pitch that is tighter than each of the plurality of cells within the second section, Additionally, a proximal end of the second section comprises a plurality of rounded ends formed by the plurality of intersecting elongated members. The stent graft further comprises a graft attached to the stent. The method also comprises positioning the stent graft near a sinotubular junction of the aorta. Further, the method comprises deploying the stent graft from the delivery configuration to an expanded configuration in which the stent graft expands radially outward such that the second section of the stent is disposed proximal the sinotubular junction of the aorta.

Further areas of applicability will become apparent from the description provided herein. It should be understood that the description and specific examples are intended for purposes of illustration only and are not intended to limit the scope of the present disclosure.

BRIEF DESCRIPTION OF THE DRAWINGS

Embodiments of the present invention are described below, by way of example only, with reference to the accompanying drawings, in which.

DETAILED DESCRIPTION OF THE PREFERRED EMBODIMENTS

The following description is merely exemplary in nature and is not intended to limit the present disclosure, application, or uses. It should be understood that throughout the drawings, corresponding reference numerals indicate like or corresponding parts and features. It should also be understood that various cross-hatching patterns used in the drawings are not intended to limit the specific materials that may be employed with the present disclosure. The cross-hatching patterns are merely exemplary of preferable materials or are used to distinguish between adjacent or mating components illustrated within the drawings for purposes of clarity.

In the present application, the term "proximal" when referring to a delivery device refers to a direction that is farthest away from the operator using a delivery device, while the term "distal" refers to a direction that is generally closest to the operator using the delivery device. The proximal and distal ends of a delivery device can also be referred to as the introduction end of the delivery device and the operator end of the delivery device. The operator end of the delivery device is that portion of the device that is intended to remain outside of a patient during a procedure. When referring to the prosthesis itself relative to the delivery device, the proximal end of the prosthesis is that part of the prosthesis nearest the delivery end of the delivery device and the distal end of the prosthesis is that end that is closest to the operator end of the delivery device. When referring to the prosthesis relative to placement in the human body, the ends of the various devices and parts of devices may be referred to as the inflow end (that end that receives fluid first), and the outflow end (that end from which the fluid exits).

Figure 1:
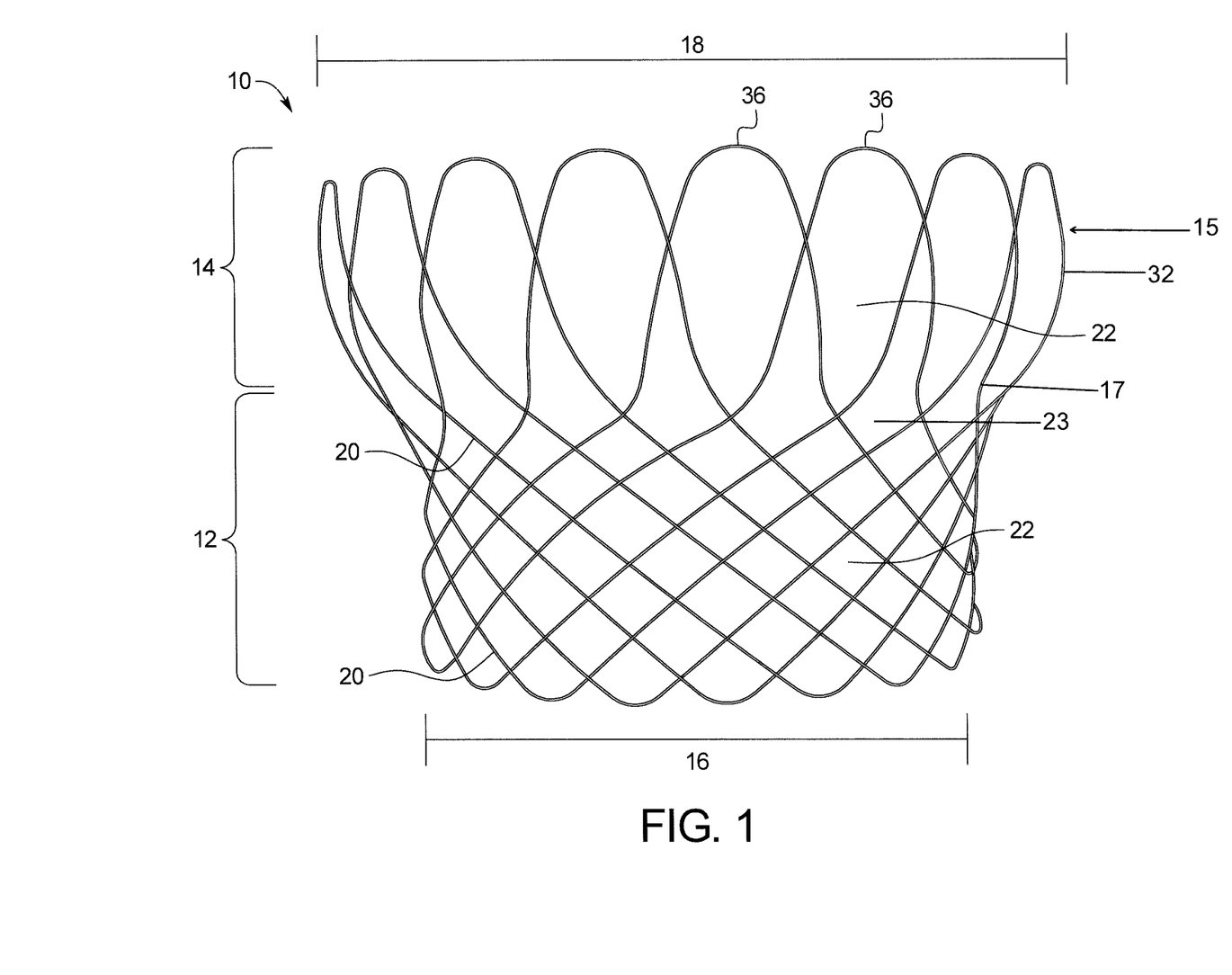
FIG. 1 is a partial side view of a stent in accordance with the teachings of the present disclosure.

FIG. 1 shows a partial view a stent 10. The stent 10 may include two sections, a first section 12 and a second section 14. The first section 12 may have a substantially constant outer diameter 16. The second section 14 may transition from the constant outer diameter 16 of the first section 12 to a larger outer diameter 18. The transition in the second section 14 from the smaller outer diameter 16 to the larger outer diameter 18 may be gradual as shown in FIG. 1. Further, the transition in the second section 14 from the smaller diameter 16 to the larger outer diameter 18 may be substantially or wholly continuous. For example, as shown by the partial profile of the stent 10 in FIG. 2, a first, concave curvature 30 may begin the transition from the smaller outer diameter 16 towards the larger outer diameter 18. Then, a second, convex curvature 32 may transition from the first, concave curvature 30 to the larger outer diameter 18. In the example of FIG. 1, the second section 14 has a first tier 15 of elongate cells, each having a rounded proximal apex 36, and a second tier 17 overlapping the first tier 15. The elongate cells of the first tier may have an upside down teardrop shape. The elongate cells 23 of the second tier 17, may have two long sides adjacent the cells of the first tier and two short sides adjacent cells of the first section 12. The first section 12 has multiple tiers of diamond shaped cells.

Figure 3:
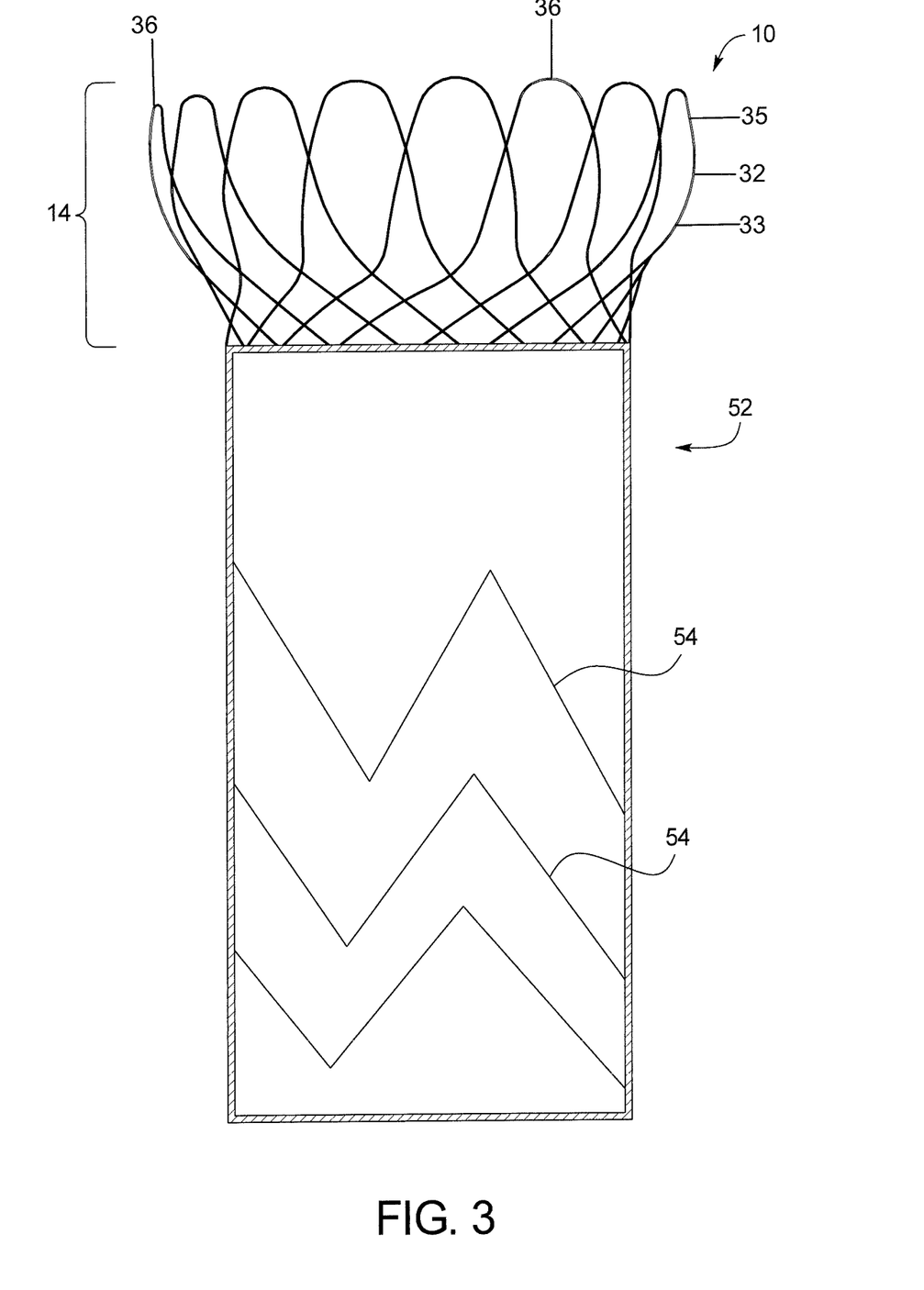
FIG. 3 is a side view of a stent graft.
Figure 6:
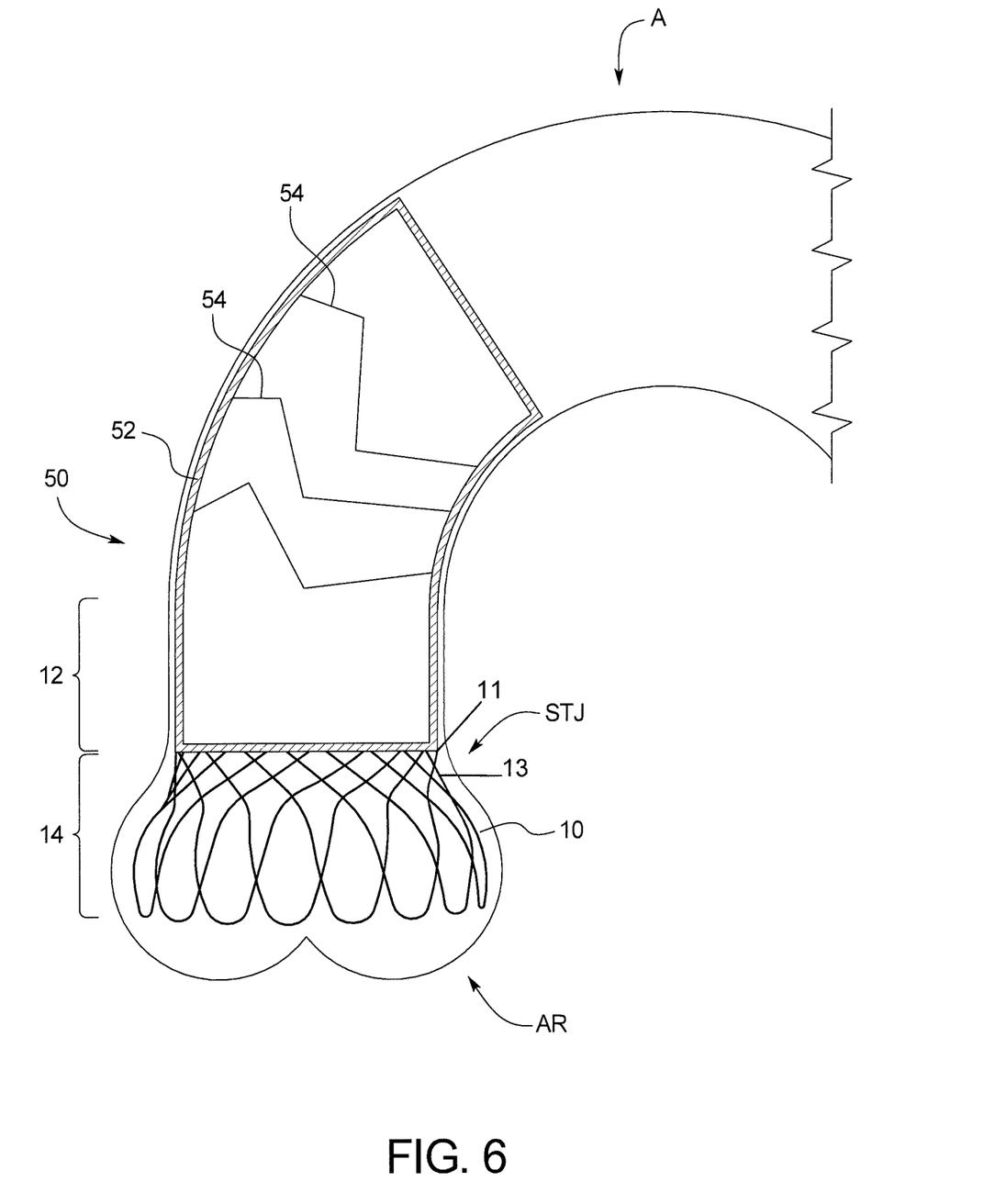
FIG. 6 is another view of a stent graft in use in a body lumen.
Figure 7:
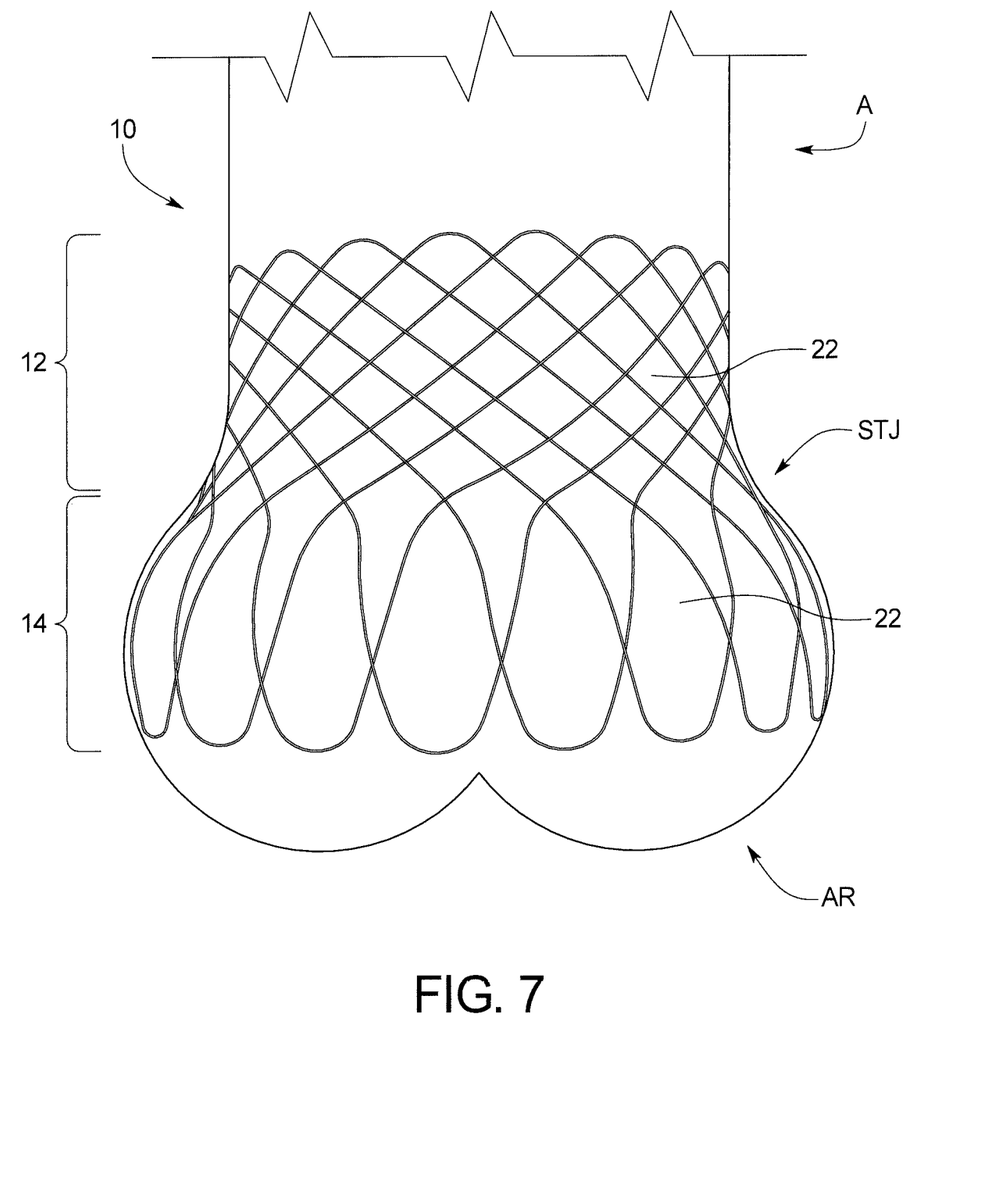
FIG. 7 is a partial view of a stent in use in a body lumen with the graft omitted for clarity.

As shown in FIGS. 1 and 3, the convex curvature has two inward curves 33, 35 so that the diameter of the mid-section of the convex curvature 32 is greater than the diameter of the diameters at the points of the inward curves 33, 35. In this way, the rounded proximal apices 36 bend or point inwardly so that the proximal end of the stent conforms to the vessel as shown in FIGS. 6 and 7.

Figure 2:
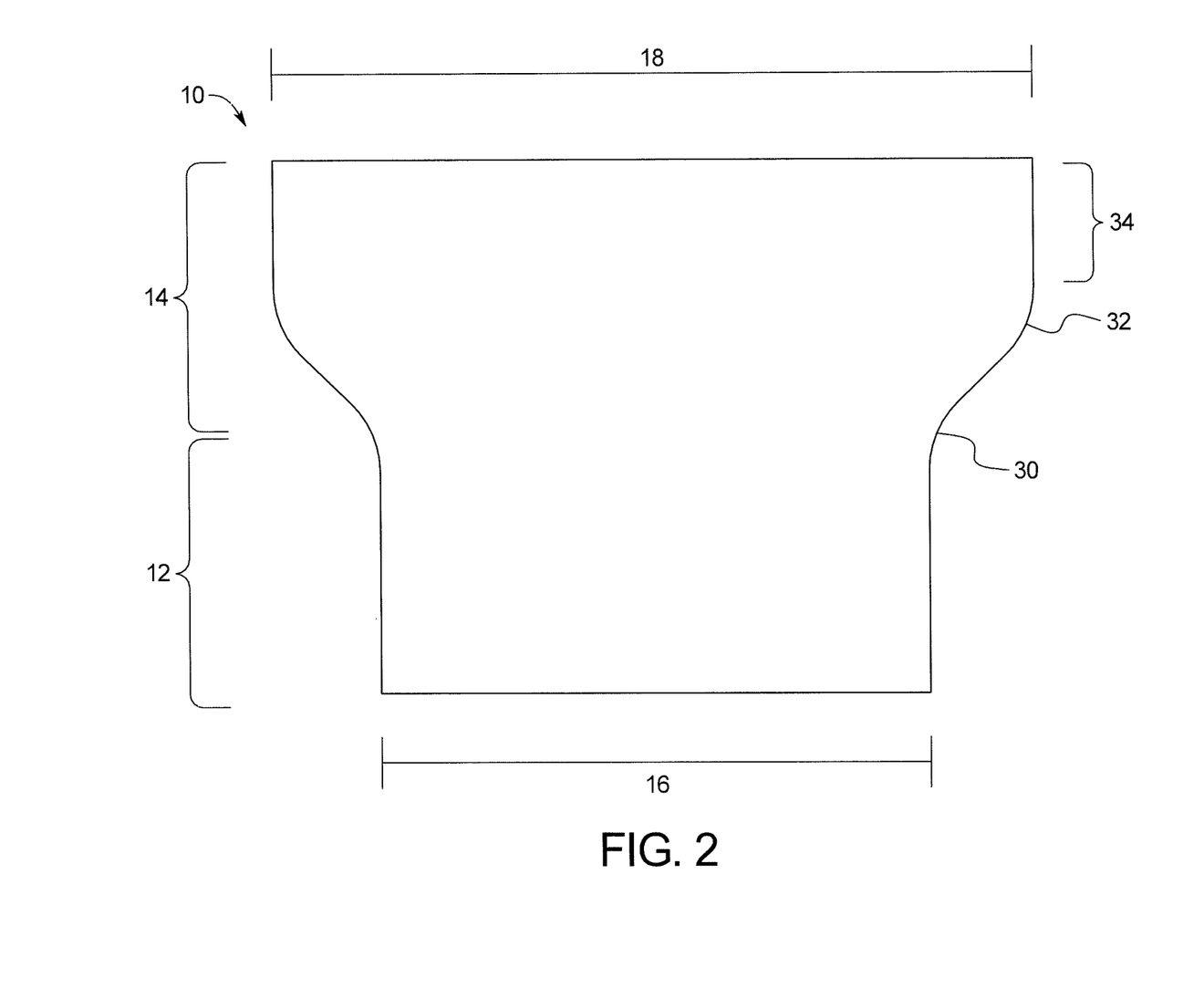
FIG. 2 is a partial profile view of a stent.

Alternatively, as shown in FIG. 2, the second section 14 may include an end portion 34 extending from one end of the second, convex curvature 30 and having a substantially constant outer diameter 18. While the first and second sections 12, 14 of the stent 10 in the present embodiment are arranged as described above, the stent 10 is not limited to this shape. For example, the stent 10 may further include a third or even fourth section of varying diameter. Further, the transition from the first section 12 to the second section 14 may vary, including a stepped transition. In each embodiment, the stent is non-cylindrical.

Referring back to FIG. 1, the stent 10 may be made of a series of intersecting wires or elongated members 20 connected to each other that form cells 22 of varying sizes and shapes. For example, the stent 10 may be braided. The size of the cells 22 may be varied by changing how closely together the elongated members 20 are assembled. Assembling the elongated members 20 closely together results in smaller cells 22, otherwise known as a tighter pitch. Conversely, assembling the elongated members 20 further apart results in larger cells 22, otherwise known as a looser pitch. By varying the size of the cells 22, the properties of the stent 10 may be varied. For example, cells 22 with a tighter pitch may have a greater radial force, thus allowing those cells 22 to provide more support to a body lumen. On the other hand, cells 22 with a looser pitch have a lesser radial force. However, cells 22 with a looser pitch allow a stent to elastically compress and expand between a larger outer diameter and a smaller outer diameter when compared to cells 22 with a tighter pitch, thus allowing the stent to be compressed into a delivery configuration with a smaller overall profile.

As shown, the cells 22 in the first section 12 are smaller than the cells 22 in the second section 14. The tighter pitch in the first section 12 allows for a greater radial force, thus providing additional radial support to the body lumen along the length of the first section 12. Since the second section 14 expands to a greater outer diameter 18 than the first section 12, a looser pitch allows the second section 14 to be radially compressed more easily into a delivery configuration. The ends 36 of stent 10 may be rounded, thus limiting any potential puncturing of, or other trauma to, the walls of the body lumen. Although the first section 12 of the stent 10 is described as having a tighter pitch than the second section 14, this is only one example of varying cell size to achieve a varying pitch. A variety of other pitch variation along the length of the stent 10 is contemplated.

The portion of the stent 10 shown may be only one portion of a stent graft system. For example, as shown in FIG. 3, a stent graft 50 may include the stent 10, a graft 52, and a body stent 54. The graft 52 may be a generally cylindrical piece of material that has a lumen (not shown) running therethrough. The first section 12 of the stent 10 (not shown in FIG. 3) may be disposed within the lumen of the graft 52 while the second section 14 of the stent 10 may extend outside of the lumen of the graft 52. The first section 12 of the stent 10 may be sewn onto or otherwise attached to the graft 52. While the first section 12 of the stent 10 shown in FIG. 3 is disposed within the lumen of the graft 52, it may also be attached to the outside surface of the graft 52 as well.

The body stent 54 may be a variety of stent designs, including but not limited to: Z-stents, annular stents, and helical stents. The body stent 54 may be sewn or otherwise attached to the graft 52, either within or outside of the lumen of the graft 52. While this embodiment describes a stent graft 50 with a separate stent 10 and body stent 54, the system could also include a single stent with the properties of both the stent 10 and body stent 54 rather than two separate stents. The proximal edge 11 of the graft 52 aligns at or adjacent the transition 13 between the first and second sections 12, 14. As shown in FIG. 6, the edge 11 of the graft aligns just below the transition 13 between the first section 12 and the second section 14. The cross link pattern of the mesh provides constant pressure along the graft edge 11 to prevent graft infolding, and therefore prevent endoleaks.

The entire stent graft 50, in use, may be moved between a delivery configuration in which the stent graft 50 is radially compressed (FIG. 4) to an expanded configuration in which the stent graft 50 is radially expanded (FIG. 3). The stent graft 50 in the present embodiment may be self-expanding, meaning the stent graft's 50 natural state is the expanded configuration. The stent graft 50 is then elastically, radially compressed to the delivery configuration via a delivery device. When the delivery device is removed from the stent graft 50, the stent graft 50 naturally expands back to the expanded configuration. While the present embodiment utilizes self-expanding properties, other stents may be used, including balloon-expandable stents.

The stent 10 and body stent 54 may each be made of a variety of biocompatible materials, including but not limited to: stainless steel, nitinol, or cobalt-chrome alloys, amorphous metals, tantalum, platinum, gold, titanium, and non-metallic materials such as thermoplastics and other polymers. The graft 52 may be made of a variety of biocompatible materials, including but not limited to: expanded polytetrafluoroethylene (ePTFE), polytetrafluoroethylene (PTFE), silicone, polyurethane, polyamide (nylon), as well as other flexible biocompatible materials. The graft 52 also can be made of known fabric graft materials such as woven polyester, polyetherurethanes, or polyethylene. The graft 52 also may include a bioremodelable material such as reconstituted or naturally-derived collagenous materials, extracellular matrix (ECM) material, submucosa, renal capsule membrane, dermal collagen, dura mater, pericardium, fascia lata, serosa, peritoneum or basement membrane layers, or intestinal submucosa, including small intestinal submucosa (SIS), stomach submucosa, urinary bladder submucosa, uterine submucosa, or other suitable materials.

Figure 4:
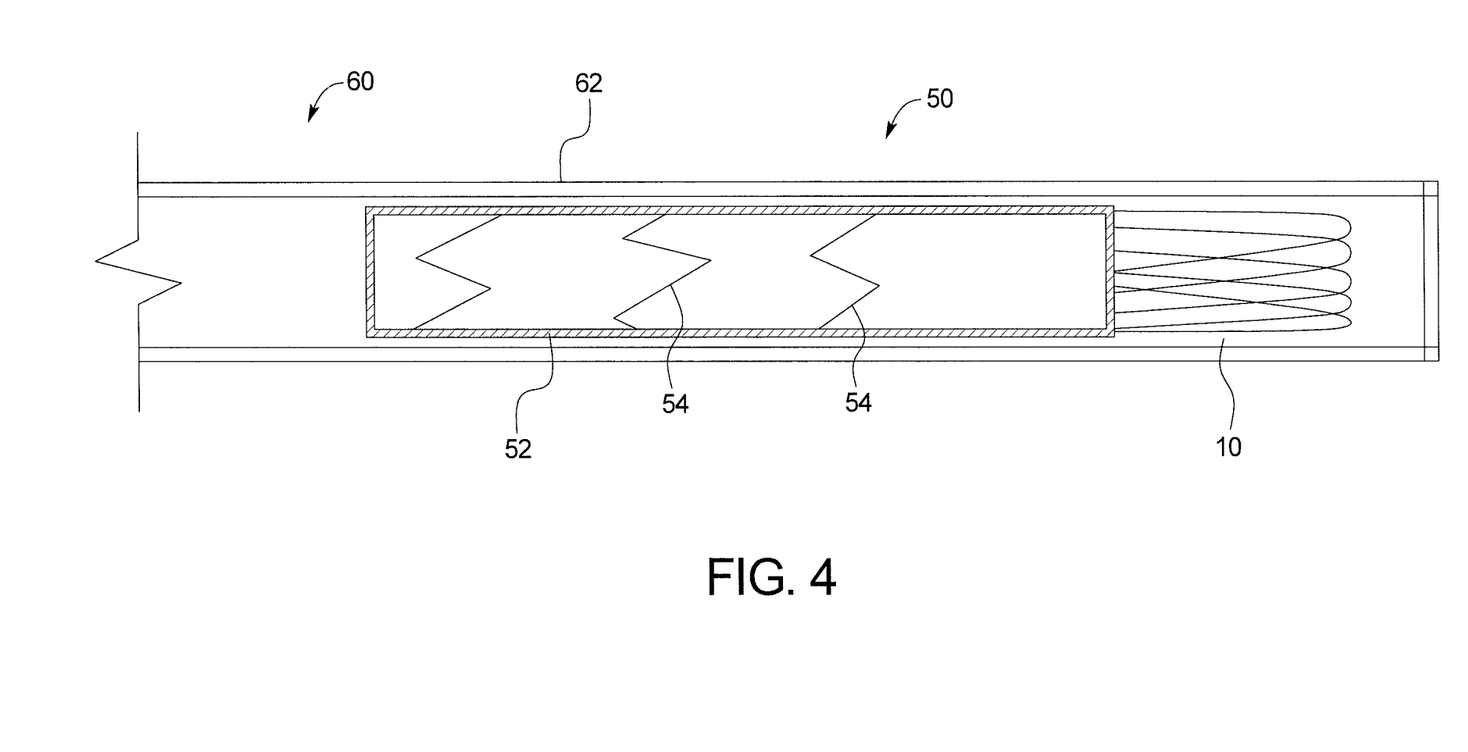
FIG. 4 is a side view of a stent graft with a delivery system.

In use, the stent graft 50 may be radially compressed into the delivery configuration via a delivery system 60 as shown in FIG. 4. The delivery system 60 may include a wide variety of stent delivery mechanisms; however, in this exemplary embodiment the delivery system 60 includes a retractable catheter 62 with a within which lumen the stent graft 50 is held in the delivery configuration. The stent graft 50 may be disposed at the proximal end of the lumen of the catheter 62.

Figure 5:
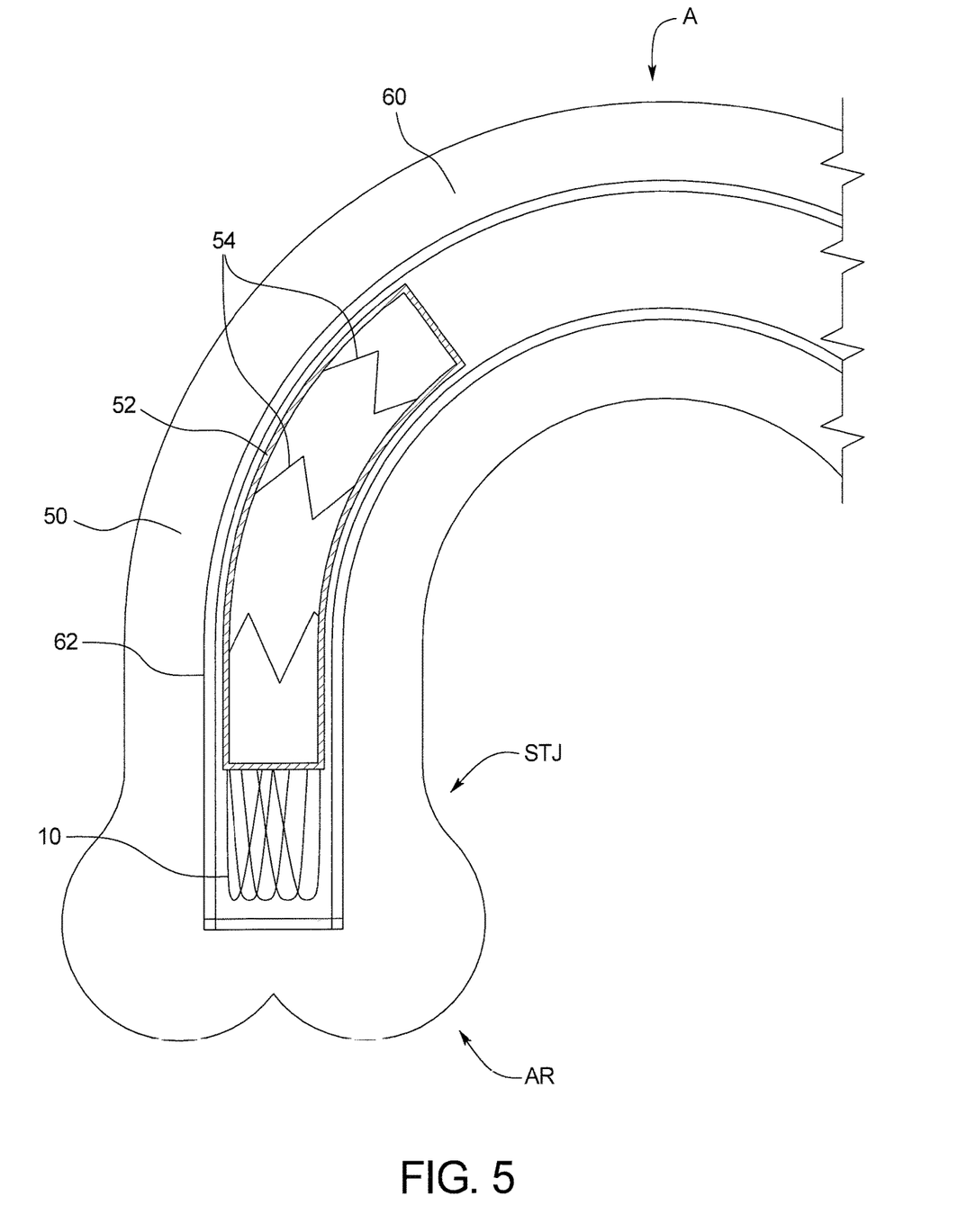
FIG. 5 is a view of a stent graft in use in a body lumen.

The physician may then access a patient's aorta A through a variety of methods, such as the well-known Seldinger technique. For example, the physician may insert the delivery system 60 with the stent graft 50 into the femoral artery. The stent graft 50 and delivery system 60 may then be advanced along the femoral artery towards the heart. Eventually the proximal end of the delivery system 60 will reach the ascending aorta as shown in FIG. 5. The delivery system 60 may be positioned such that the second section 14 of the stent 10 is positioned just proximal to the sinotubular junction STJ and extending into the aortic root AR. The first section 12 of the stent 10 along with the rest of the stent graft 50 may therefore be positioned to extend just distal to the sinotubular junction STJ into the ascending aorta.

Next, the delivery catheter 62 may be retracted distally while the stent graft 50 is maintained in position, thus freeing the stent graft 50 from the confines of the delivery catheter 62 and allowing the stent graft 50 to expand as shown in FIG. 6. As can be seen in FIG. 6 (and in FIG. 7 showing the stent 10 without the graft 52 and body stent 54), the second section 14 of the stent 10 expands into the aortic root AR, thus allowing the entire stent graft 50 to be more securely placed near the sinotubular junction STJ with limited fear of migration. Further, since the graft 52 does not extend through the second section 14 of the stent 10, the enlarged cells 22 of the second section 14 allow for sufficient blood profusion to the coronary arteries, whereas smaller cells may cause undesirable blockage in the aortic root AR. Since the first section 12 of the stent 10 has a tighter pitch, the accompanying greater radial force allows the stent graft 50 to sufficiently support the weakened or ruptured section of the aorta A. Further, since the graft 52 extends distally from the sinotubular junction STJ, the graft 52 may provide the necessary sealing for an aneurysm or dissection right at or near the sinotubular junction STJ.

It will be appreciated that in place of changing pitch angle to change radial expansion force, other provisions may be used, such as using elongate elements 20 of different material and/or thickness to achieve a desired change in expansion force.

While the embodiments disclosed above are primarily discussed for use in the aorta and particularly near the sinotubular junction of the aorta, the disclosure is not so limited. The embodiments may be used in a variety of ways and in a variety of body lumens as desired.

The description of the disclosure is merely exemplary in nature and, thus, variations that do not depart from the substance of the disclosure are intended to be within the scope of the disclosure. Such variations are not to be regarded as a departure from the spirit and scope of the disclosure.

The invention claimed is:
1. A stent, comprising:
a plurality of intersecting elongated members arranged to form a plurality of cells, at least some of the plurality of cells forming a tube with a lumen running therethrough, wherein the tube comprises first and second sections, the first section having a substantially constant first diameter, the second section having a second diameter that is larger than the first diameter, the tube comprising a transition section between the first and second sections, the transition section having a concave curvature extending proximally from the first section toward the second section and a convex curvature extending proximally from the concave curvature to the second section, wherein the second section has a first tier of elongate cells of the plurality of elongate cells having a first shape and rounded proximal apices and a second tier of elongate cells of the plurality of cells having a second shape different from the first shape,
wherein the first section has multiple tiers of diamond shaped cells of the plurality of cells, the multiple tiers each having a length less than each of the first and second tiers of elongate cells,
wherein the first section exhibits a greater force of radial expansion than the second section, and wherein the rounded proximal apices of the first tier extend inwardly toward a center of the stent.

2. The stent of claim 1, wherein each of the plurality of cells within the first section have a pitch that is tighter than each of the plurality of cells within the second section.

3. The stent of claim 1, wherein the second section comprises a convex curvature from a distal end of the second section to a proximal end of the second section, such that the second section is non-cylindrical.

4. The stent graft of claim 3, wherein the second section comprises a mid-section between the distal end and the proximal end, wherein the mid-section has a diameter that is greater than the diameter of the stent distal end of the second section and the proximal end of the second section.

5. The stent of claim 1, wherein the elongate cells of the first tier have a reverse teardrop shape.

6. The stent of claim 5, wherein the elongate cells of the second tier have a distorted diamond shape with two long sides each adjacent an elongate cell of the first tier and two short sides each adjacent a cell of the first section.

7. The stent of claim 1, comprising a tube of graft material attached to a portion of the stent and forming a stent graft.

8. The stent graft of claim 7, wherein the tube of graft material has a proximal edge disposed adjacent the transition section.

9. The stent graft of claim 8, wherein the tube of graft material does not extend beyond the transition section.

10. The stent graft of claim 7, wherein the first section has a length and the second section has a length less than the length of the first section and the tube of graft material covers the length of the first section and extends distally beyond a distal end of the first section.

11. The stent graft of claim 10, wherein the stent is a first stent and the stent graft further comprises at least one second stent attached to the tube of graft material and disposed distally of the first stent, the second stent having a configuration different from the first stent.

12. The stent graft of claim 11, wherein the at least one second stent comprises a plurality of discrete stents disposed along a length of the tube of graft material.

13. A stent graft, comprising:
a tube of graft material having an inner lumen;
a non-cylindrical stent attached to the graft comprising a plurality of intersecting elongated members arranged to form a plurality of cells, the plurality of cells forming a tube with a lumen running therethrough,
wherein the tube comprises first and second sections, the first section having a substantially constant first diameter, the second section having a second diameter that is larger than the first diameter, the tube comprising a transition section between the first and second sections, the transition section having a concave curvature extending proximally from the first section toward the second section and a convex curvature extending proximally from the concave curvature to the second section,
wherein the second section has a first tier of elongate cells of the plurality of elongate cells having a first shape and rounded proximal apices and a second tier of elongate cells of the plurality of cells having a second shape different from the first shape,
wherein the first section has multiple tiers of diamond shaped cells of the plurality of cells, the multiple tiers each having a length less than each of the first and second tiers of elongate cells,
wherein the first section exhibits a greater force of radial expansion than the second section, and wherein the second section comprises a mid-section between the distal end and the proximal end, wherein the mid-section has a diameter that is greater than the diameter of the stent distal end of the second section and the proximal end of the second section, and
wherein the rounded proximal apices of the first tier extend inwardly toward a center of the non-cylindrical stent; and
a cylindrical stent disposed distally of the first stent and having a configuration different from the first stent.

14. The stent graft of claim 13, wherein each of the plurality of cells within the first section have a pitch that is tighter than each of the plurality of cells within the second section.

15. The stent graft of claim 13, wherein the second section comprises a convex curvature from a distal end of the second section to a proximal end of the second section.

16. The stent graft of claim 15, wherein the second section comprises a mid-section between the distal end and the proximal end, wherein the mid-section has a diameter that is greater than the diameter of the stent distal end of the second section and the proximal end of the second section.

17. The stent graft of claim 13, wherein the elongate cells of the first tier have a reverse teardrop shape.

18. The stent graft of claim 17, wherein the elongate cells of the second tier have a distorted diamond shape with two long sides each adjacent an elongate cell of the first tier and two short sides each adjacent a cell of the first section.

19. The stent graft of claim 13, wherein the tube of graft material has a proximal edge disposed adjacent the transition section.

20. The stent graft of claim 19, wherein the tube of graft material does not extend proximally beyond the transition section.

21. The stent graft of claim 20, wherein the at least one cylindrical stent comprises a plurality of discrete cylindrical stents disposed along a length of the tube of graft material.

22. The stent graft of claim 13, wherein the second section comprises a continuous curve from the distal end of the second section to the proximal end of the second section.

23. A stent graft, comprising:
a stent, comprising:
a plurality of intersecting elongated members arranged to form a plurality of cells, at least some of the plurality of cells forming a tube with a lumen running therethrough, wherein the tube comprises first and second sections, the first section having a substantially constant first diameter, the second section having a second diameter that is larger than the first diameter, the tube comprising a transition section between the first and second sections, the transition section having a concave curvature extending proximally from the first section toward the second section and a convex curvature extending proximally from the concave curvature to the second section, wherein the second section has a first tier of elongate cells of the plurality of elongate cells having a first shape and rounded proximal apices and a second tier of elongate cells of the plurality of cells having a second shape different from the first shape,
a tube of graft material attached to a portion of the stent,
wherein the first section has multiple tiers of diamond shaped cells of the plurality of cells, the multiple tiers each having a length less than each of the first and second tiers of elongate cells,
wherein the first section exhibits a greater force of radial expansion than the second section, and wherein the rounded proximal apices of the first tier extend inwardly toward a center of the stent, wherein the elongate cells of the second tier are adjacent cells of the first tier and are adjacent cells of the first section, wherein the tube of graft material has a proximal edge disposed at or adjacent the transition section.

24. The stent graft of claim 23, wherein each of the plurality of cells within the first section have a pitch that is tighter than each of the plurality of cells within the second section and the transition section comprises a change in pitch from the pitch of the cells of the first section to a pitch of the cells of the second section and the proximal edge of the tube of graft material is disposed at the change in pitch.

* * * * *